United States Patent [19]
Kaufman et al.

[11] Patent Number: 5,168,548
[45] Date of Patent: Dec. 1, 1992

[54] INTEGRATED VOICE CONTROLLED REPORT GENERATING AND COMMUNICATING SYSTEM

[75] Inventors: Steven Kaufman, Boston; James Moser, Dorchester; Ronald N. Parente, Bolton, all of Mass.

[73] Assignee: Kurzweil Applied Intelligence, Inc., Waltham, Mass.

[21] Appl. No.: 525,079

[22] Filed: May 17, 1990

[51] Int. Cl.⁵ .................... G10L 9/00; H04M 11/00
[52] U.S. Cl. .............................. 395/2; 358/434
[58] Field of Search ....................... 381/41–45; 364/513.5; 358/434, 438, 440; 379/100

[56] References Cited

U.S. PATENT DOCUMENTS

| | | | |
|---|---|---|---|
| 4,764,965 | 8/1988 | Yoshimura et al. | 381/43 |
| 4,779,209 | 10/1988 | Stapleford et al. | 364/513.5 |
| 4,827,520 | 5/1989 | Zeinstra | 381/41 |
| 4,829,576 | 5/1989 | Porter | 381/43 |
| 4,847,906 | 7/1989 | Ackenhusen | 381/41 |
| 4,931,950 | 6/1990 | Isle et al. | 364/513 |
| 5,073,921 | 12/1991 | Nomura et al. | 381/43 |

Primary Examiner—Michael R. Fleming
Assistant Examiner—Michelle Doerrler
Attorney, Agent, or Firm—Henry D. Pahl, Jr.

[57] ABSTRACT

In the reporting system disclosed herein, a speech recognizer is used to select sections of text from a report form stored in a computer and to insert recognized terms in the text thereby to generate a report text under voice control. A command interpreter, also responsive to spoken words, initiates creation of the report text and its subsequence storing, printing and transmission. The command processor is responsive to respective spoken commands to select a destination telephone number and to cause the report text to be sent to apparatus for converting report text to image data and for modulating an audio band signal with the image data for facsimile transmission over telephone lines.

3 Claims, 2 Drawing Sheets 5,168,548

INTEGRATED VOICE CONTROLLED REPORT GENERATING AND COMMUNICATING SYSTEM

BACKGROUND OF THE INVENTION

The present invention relates to a reporting system and more particularly to a reporting system which employs a speech recognition means to enable a user to generate a complete report text and transmit that text to a selected recipient under voice control.

Particularly in certain medical situations, the creation and delivery of technical reports has presented difficulty both in terms of the time and expense involved and in the accuracy, completeness, and timeliness of the reports. Even if the report is generated in a prompt and accurate manner, delivery of the report to the desired recipient has often been a stumbling block, even when conventional facsimile machines were available to transmit a hard copy from the author to the recipient. It is, for example, highly desirable that the determinations made by a radiologist examining x-rays be made promptly available to the referring physician.

Among the several objects of the present invention may be noted the provision of a novel system for creating and delivering reports; the provision of such a system which permits reports to be generated quickly and accurately; the provision of such a system which allows reports to be delivered to a selected recipient promptly after the creation of the report; the provision of such a system which does not require the manual entering of substantial quantities of text; the provision of such a system which is highly reliable and which is of relatively simple and inexpensive construction. Other objects and features are in part apparent and in part will be pointed out hereinafter.

SUMMARY OF THE INVENTION

In a reporting system in accordance with the present invention, a speech recognition means provides a plurality of vocabulary action tables (VATs) which relate trained utterances to corresponding program input data elements. A command interpreter responsive to a first one of the VATs selectively initiates creation of a report text and the storing, printing and transmitting of report texts. A stored report form provides selectable sections of text and selectable text insertions, respective ones of the VATs providing keyword selection of text sections and of text insertions. The system also includes means for converting text to image data and for modulating an audio band signal with the image data for facsimile transmission. A further VAT relates trained utterances to stored telephone numbers, and the command interpreter is operative, in response to a respective spoken command, to cause the sending of a selected telephone number to a telephone dialing means and to cause the sending of generated report text to the converting and modulating means.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
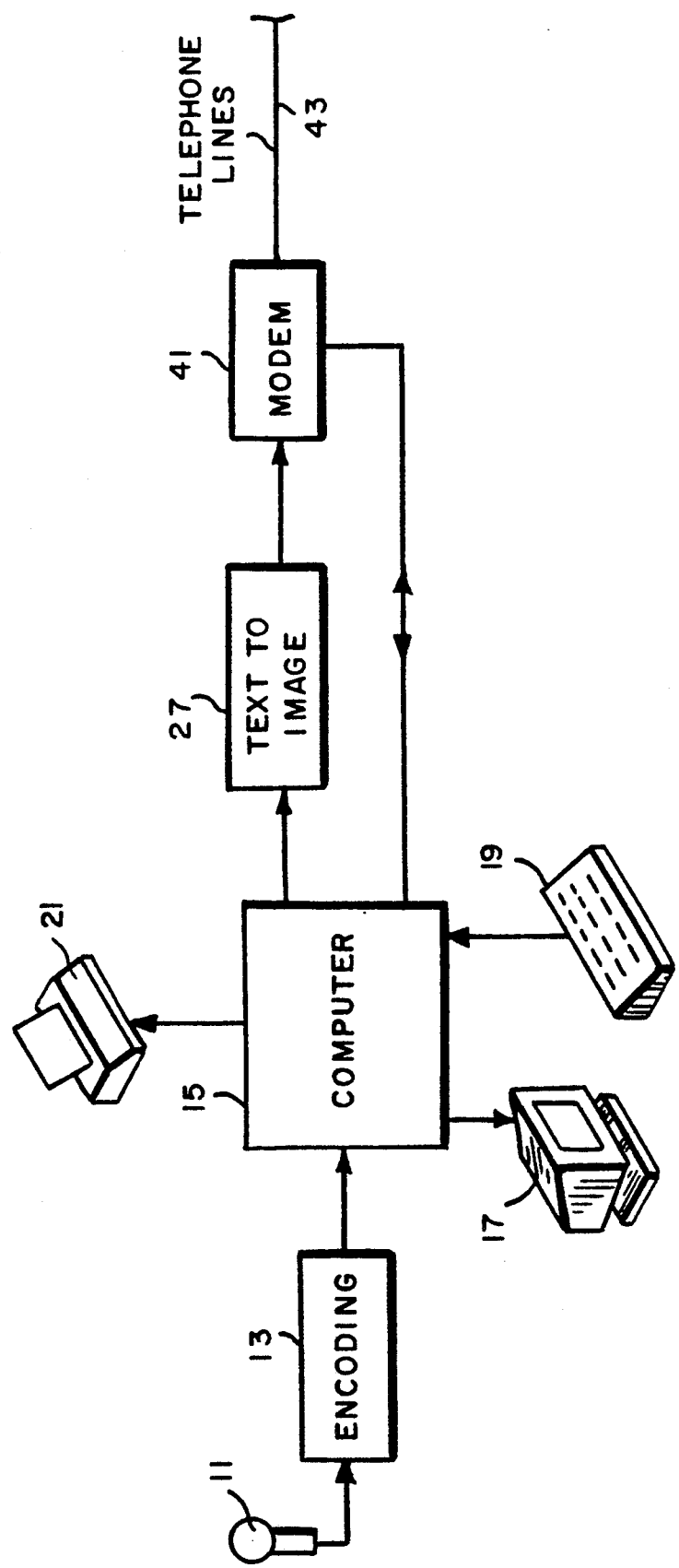
FIG. 1 is a block diagram illustrating the interconnection of the various elements of a reporting system in accordance with the present invention.

Referring now to FIG. 1, an audio signal obtained from a microphone 11 is provided to so-called front end processing circuitry 13 which performs an initial spectral analysis and encoding of the raw audio signal. The circuitry 13 generates, for each spoken word, a succession of encoded data frames which are provided to a general purpose programmed computer, designated by reference character 15. Various types of encoding are known in the art.

The computer 15 may, for example, be one of the well known types which utilizes the Intel 80386 processor and operates under the MS-DOS operating system. Though shown physically separated, the encoding circuitry 13 may in practice be implemented on a card included in the computer which the processor accesses through a bus structure. As is understood, such computers normally include a so-called hard disk rotating memory for storing the large quantities of data which are typically associated with speech recognition systems.

In particular, the computer 15 stores a large number of digitally encoded speech reference samples, each of which comprises a series of data frames derived from a training session during which the user speaks words or phrases to be included within the speech recognition system's vocabulary. To increase the likelihood of recognition, multiple representative reference samples may be provided for a single vocabulary word. A video terminal 17 and a keyboard 19 are provided for user interaction with the computer. Also conventionally, there is associated with the computer a printer 21. Printer 21 is preferably of a type which can print graphics characters as well as alphanumeric characters.

In order to constrain the number of possible vocabulary choices which need to be examined at various points in the process of generating a report and also to allow different translations at different times, the samples are preferably organized in vocabulary action tables (VATs) corresponding to the possible courses of action which may be taken at various junctures in the running of the report generation system. Each vocabulary action table relates trained utterances or reference samples to corresponding program input data elements, i.e. data strings which can control or act as responses to the computer system just as data strings entered from the keyboard 19 may provide such input elements.

Depending upon the state of the computer program, the program input elements generated in response to spoken utterances can be used for various purposes. As is conventional, the report generating program will include some form of command interpreter for selectively initiating various operations in the embodiment illustrated such operations include the initial creation of a report text and storing, printing and transmitting of such report texts. The command interpreter is responsive to a respective VAT as well as to input from the keyboard 19.

Generation of a report is facilitated by utilizing a stored report form which provides a large number of selectable sections of text and context based sets of words or texts that can be inserted in blanks left in the form. Selection of words to fill in blanks in the text is made by the speech recognition system utilizing a corresponding VAT. Appropriate sections of text are likewise selected by voice command, again using data from a respective VAT which is activated when the selection is applicable.

The setting up of standard report forms and the defining of suitable VATs for controlling the selections is preferably performed using the knowledge base editor available from Kurzweil Applied Intelligence of Waltham, Mass.. Particular medical applications are marketed by Kurzweil Applied Intelligence under the trademark "VOICEMED" and Kurzweil also markets front end signal processing such as that indicated by reference character 13 in a card form which is readily installable in IBM PC compatible computers of the type described hereinbefore using the Intel 80386 processor.

The report text generated by the VOICEMED systems are in ASCII text form. To facilitate the transmission of the reports generated to standard facsimile machines which are in wide spread use, the system of FIG. 1 incorporates circuitry and software for converting the text to a corresponding image, e.g. using character generating read only memories (ROMS) such as are commonly used in printers and video displays as well. Image data is provided to a modem 41 which is operated under the control of the computer 15. The modem 41 modulates an audio signal in correspondence with the image data and implements facsimile transmission of the data over telephone lines as indicated by reference character 43.

Circuitry suitable for performing the text to image data and for implementing the mode functions is manufactured and sold by the Quadram Corporation of Norcross, Ga. under the model designation JT FAX 9600. This circuitry is also provided on a circuit card suitable for inclusion in an IBM-PC compatible computer of the type described previously, although it is shown as physically separate in the diagram of FIG. 1. The Quadram product also incorporates circuitry for dialing telephone numbers provided to it by the computer processor and for signalling to the processor when a connection is established.

In addition to the VATs associated with the text selection and blank filling in, the system of the present invention also incorporates a VAT which relates trained utterances to stored telephone numbers. Thus, by speaking a name or other designator associated with a desired recipient, a user of the system can select that person or place to receive a copy of the report. The command interpreter VAT likewise includes entries which cause the selected telephone number to be applied to the modem and, upon establishment of the desired telephone connection, the initiation of transmission of the report text to the converting circuitry 27 and thence to the modem 41.

From the foregoing, it can be seen that a user can generate and transmit a technical report as essentially a single operation without requiring extensive entry of text or commands through a keyboard and without the usual step of printing out the report and then manually transferring it to a conventional fax machine for transmission to the desired recipient.

Figure 2:
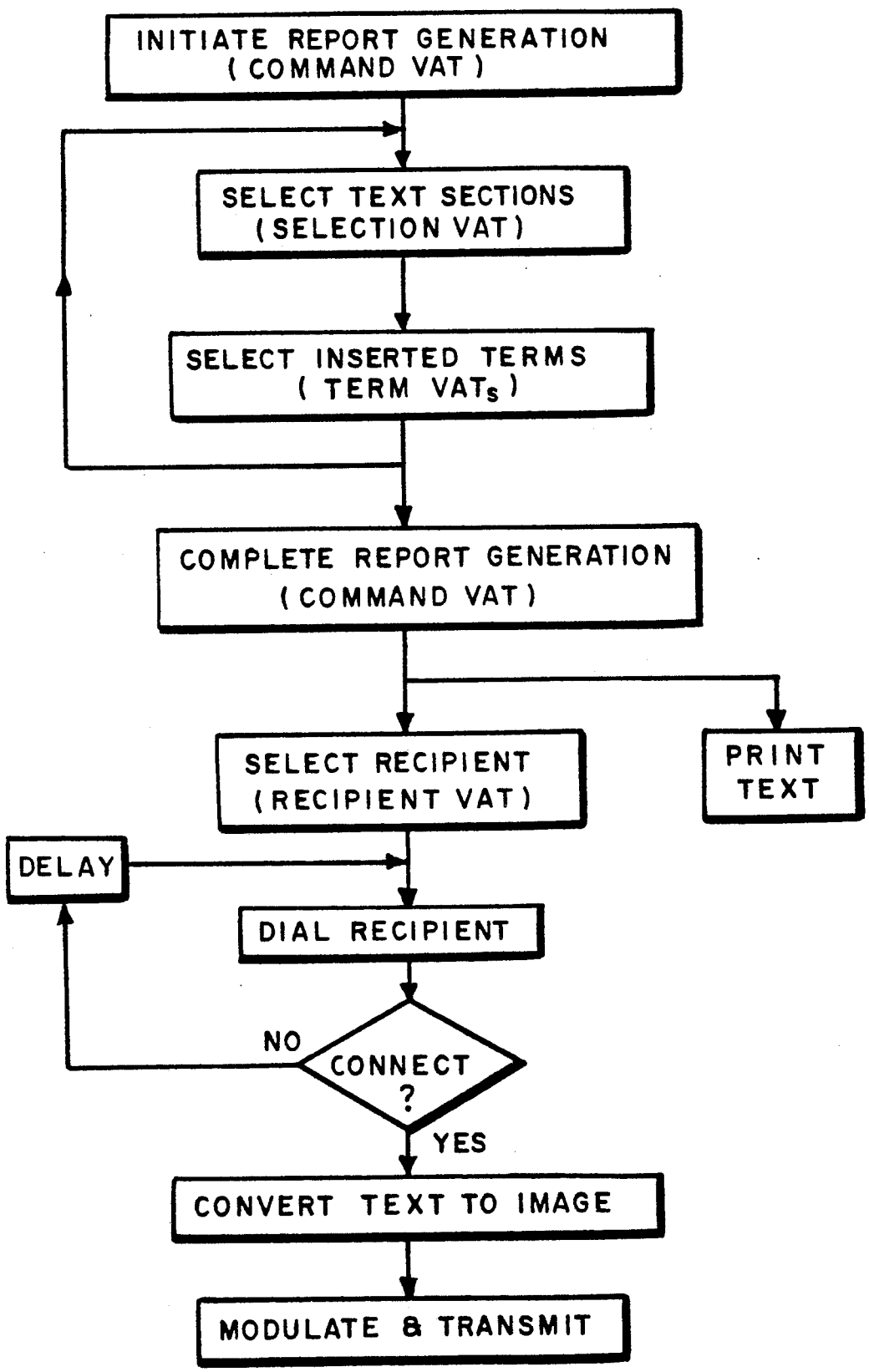
FIG. 2 is a flowchart illustrating the operation of the reporting system.

A typical sequential set of operations is illustrated in FIG. 2. Utilizing the COMMAND VAT, the user can initiate generation of a report and once the standard report form is loaded, the user can select appropriate text sections under the using words or phrases stored in the SELECTION VAT. Similarly, in each text section, terms or phrases for filling in blanks can be selected using respective TERM VATs. When the report is in a form suiting the user, he can designate that the report generation is complete by speaking in an appropriate COMMAND utterance. If desired, a hard copy of the report can be generated locally at the printer 21 and, at essentially the same time, the user can request that the text of the report be sent by facsimile and by voice command can select a recipient from entries in the corresponding RECIPIENT VAT. Upon being provided with a telephone number, the modem 41 preferably initiates dialing on a repeating basis at timed intervals until a connection is made at which point it signals back to the computer that the connection is established and the computer, in turn, initiates transferring of the report text in ASCII form to the converting circuitry 27 which in turn provides image data to the modem for facsimile transmission. While the conversion of ASCII text to image data is preferably performed just prior to transmission, it should be understood that image data could be generated earlier, e.g. as part of the report generation process. Further, other image data such as charts, graphs, x-rays, CAT scans or other digital images could be merged with the associated text for transmittal as an integrated document.

Accompanying this specification is an appendix which includes a listing of computer program components, written in the "C" programming language, which implement the report transmission functions and which can be incorporated in the Kurzweil VOICEME system described previously.

In view of the foregoing it may be seen that several objects of the present invention are achieved and other advantageous results have been attained.

As various changes could be made in the above constructions without departing from the scope of the invention, it should be understood that all matte contained in the above description or shown in the accompanying drawings shall be interpreted as illustrative and not in a limiting sense.

What is claimed is:

1. A reporting system comprising:
  speech recognition means responsive to a user's voice;
  a command interpreter responsive to said speech recognition means for selectively initiating creation of a report text in response to a respective spoken command;
  a stored report form providing selectable sections, selection of sections being controllable by said speech recognition means thereby to generate a report text under voice control;
  means for converting text to image data; and means for modulating an audio band signal with image data for facsimile transmission over telephone lines, said command interpreter being operative in response to a respective spoken command to send a report text to said converting and modulating means.

2. A reporting system comprising:
  speech recognition means responsive to a user's voice;
  a stored report form providing selectable sections of text and adapted to receive selectable text insertions, selections being controllable by said speech recognition means thereby to generate a report text under voice control;
  a command interpreter responsive to said speech recognition means for selectively initiating creation of a report text and for storing, printing and transmitting report texts so created in response to respective spoken commands;
dialing means for dialing telephone numbers;
means for converting text to image data; and
means for modulating an audio band signal with image data for facsimile transmission over telephone lines, said command interpreter being operative in response to a respective spoken command to cause sending of a telephone number selected through said speech recognition means to said dialing means and to cause sending of generated report text to said converting means and modulating means.

3. A reporting system comprising:
speech recognition means responsive to a user's voice and providing a plurality of Voice Action Tables (VATs) which relate trained utterances to corresponding program input data elements;
a stored report form providing selectable sections of text and adapted to receive selected text insertions, one of said VATs providing keyword recognition for selecting text sections and further ones of said VATs providing term recognition for selecting text insertions thereby to generate a report text under voice control;
a command interpreter responsive to another one of said VATs for selectively initiating creation of a report text and for storing, printing and transmitting report texts so created in response to a respective spoken command;
dialing means for dialing telephone numbers;
means for converting text to image data;
means for modulating an audio band signal with image data for facsimile transmission over telephone lines; and
a recipient VAT relating trained utterances to stored telephone numbers, said command interpreter being operative in response to a respective spoken command to cause sending of a telephone number selected through said recipient VAT to said dialing means and to cause sending of generated report text to said converting means and modulating means.

* * * * *